United States Patent [19]

Passafaro et al.

[11] Patent Number: 5,324,255

[45] Date of Patent: Jun. 28, 1994

[54] ANGIOPLASTY AND ABLATIVE DEVICES HAVING ONBOARD ULTRASOUND COMPONENTS AND DEVICES AND METHODS FOR UTILIZING ULTRASOUND TO TREAT OR PREVENT VASOPASM

[75] Inventors: James D. Passafaro, Santa Ana; Henry Nita, Lake Forest; Robert J. Siegel, Venice; Douglas H. Gesswein, Mission Viejo, all of Calif.

[73] Assignee: Baxter International Inc., Deerfield, Ill.

[21] Appl. No.: 911,651

[22] Filed: Jul. 10, 1992

Related U.S. Application Data

[63] Continuation-in-part of Ser. No. 640,190, Jan. 11, 1991, and a continuation-in-part of Ser. No. 878,795, May 5, 1992, Pat. No. 5,267,954.

[51] Int. Cl.⁵ .................................................. A61B 17/20
[52] U.S. Cl. .................................. 604/22; 604/49; 128/898
[58] Field of Search ........... 128/24 AA; 604/22, 93, 604/101; 606/169-171

[56] References Cited

U.S. PATENT DOCUMENTS

| | | | |
|---|---|---|---|
| 3,352,303 | 11/1967 | Delaney | 128/24 AA |
| 3,433,226 | 3/1969 | Boyd . | |
| 3,526,219 | 9/1970 | Balamuth . | |
| 3,565,062 | 2/1971 | Kuris | 606/169 |
| 3,589,363 | 6/1971 | Banko . | |
| 3,618,594 | 11/1971 | Banko . | |
| 3,823,717 | 7/1974 | Pohlman et al. | 604/22 |
| 3,861,391 | 1/1975 | Antonevich et al. . | |
| 3,896,811 | 7/1975 | Storz . | |
| 4,188,952 | 2/1980 | Loschilov et al. . | |
| 4,214,586 | 7/1980 | Mericle . | |
| 4,223,676 | 9/1980 | Wuchinich et al. . | |
| 4,366,819 | 1/1983 | Kaster . | |
| 4,431,006 | 2/1984 | Trimmer et al. . | |
| 4,587,958 | 5/1986 | Noguchi et al. . | |
| 4,587,972 | 5/1986 | Morantte, Jr. . | |
| 4,589,419 | 5/1986 | Laughlin et al. . | |
| 4,665,906 | 5/1987 | Jervis . | |
| 4,692,139 | 9/1987 | Stiles | 604/22 |
| 4,750,902 | 6/1988 | Wuchinich et al. . | |
| 4,794,931 | 1/1989 | Yock . | |
| 4,799,496 | 1/1989 | Hargraves . | |
| 4,800,876 | 7/1991 | Fox et al. . | |
| 4,808,153 | 2/1989 | Parisi | 604/22 |
| 4,821,731 | 4/1989 | Martinelli et al. . | |

(List continued on next page.)

FOREIGN PATENT DOCUMENTS

| | | |
|---|---|---|
| 1531659 | 7/1977 | European Pat. Off. . |
| 189329 | 7/1986 | European Pat. Off. . |
| 208175 | 1/1987 | European Pat. Off. . |
| 234951 | 2/1987 | European Pat. Off. . |
| 315290 | 10/1987 | European Pat. Off. . |
| 347098 | 6/1989 | European Pat. Off. . |
| 443256 | 12/1990 | European Pat. Off. . |
| 472368 | 2/1992 | European Pat. Off. . |

(List continued on next page.)

*Primary Examiner*—C. Fred Rosenbaum
*Assistant Examiner*—Michael Rafa
*Attorney, Agent, or Firm*—Stetina & Brunda

[57] ABSTRACT

A catheter device incorporating combined ultrasound ablation and balloon dilation components. The catheter device generally comprises an elongate catheter body having proximal and distal ends and an outer surface. Disposed on the outer surface of the catheter body is a dilation balloon. At least one balloon inflation lumen fluidly connects the proximal end of the catheter body to the dilation balloon to permit injection of inflation fluid into the dilation balloon. Extending longitudinally through the catheter body is an ultrasound transmission member having a proximal end and a distal end, with the proximal end being connectable to an ultrasound transducer such that ultrasonic energy will pass through the ultrasound transmission member to the distal end thereof. In alternative embodiments of the present invention, there are provided catheter devices incorporating combined ultrasound ablation and laser ablation components as well as combined ultrasound ablation and atherectomy ablation components.

4 Claims, 6 Drawing Sheets

U.S. PATENT DOCUMENTS

| | | |
|---|---|---|
| 4,841,977 | 6/1989 | Griffith et al. . |
| 4,844,092 | 7/1989 | Rydell . |
| 4,870,953 | 10/1989 | DonMicheal et al. ........ 128/24 AA |
| 4,898,575 | 2/1990 | Fischell et al. . |
| 4,917,097 | 4/1990 | Proudian et al. . |
| 4,919,133 | 4/1990 | Chiang . |
| 4,920,954 | 5/1990 | Alliger et al. . |
| 4,924,863 | 5/1990 | Sterzer ................................. 606/27 |
| 4,936,281 | 6/1990 | Stasz . |
| 4,957,111 | 9/1990 | Millar . |
| 4,960,411 | 10/1990 | Buckbinder . |
| 4,967,653 | 11/1990 | Hinz . |
| 4,979,939 | 12/1990 | Shiber . |
| 4,988,356 | 1/1991 | Crittenden . |
| 5,058,570 | 10/1991 | Idemoto et al. . |
| 5,061,238 | 10/1991 | Shuler . |
| 5,069,664 | 12/1991 | Guess et al. ........................... 604/22 |
| 5,076,276 | 12/1991 | Sakurai et al. . |
| 5,100,423 | 3/1992 | Fearnot . |

FOREIGN PATENT DOCUMENTS

| | | |
|---|---|---|
| 2349120 | 4/1975 | Fed. Rep. of Germany . |
| 2438648 | 2/1976 | Fed. Rep. of Germany . |
| 2453058 | 5/1976 | Fed. Rep. of Germany . |
| 2453126 | 5/1976 | Fed. Rep. of Germany . |
| 2541919 | 3/1977 | Fed. Rep. of Germany . |
| 2703486 | 12/1977 | Fed. Rep. of Germany . |
| 8119209 | 9/1981 | Fed. Rep. of Germany . |
| 3707567 | 9/1987 | Fed. Rep. of Germany . |
| 3707921 | 9/1987 | Fed. Rep. of Germany . |
| 3812836 | 4/1988 | Fed. Rep. of Germany . |
| 3826414 | 2/1989 | Fed. Rep. of Germany . |
| 2424733 | 1/1980 | France . |
| 2641693 | 7/1990 | France . |
| 2643272 | 8/1990 | France . |
| 2208138 | 3/1989 | United Kingdom . |
| 2212267 | 7/1989 | United Kingdom . |
| WO87/01276 | 3/1987 | World Int. Prop. O. . |
| WO87/05793 | 10/1987 | World Int. Prop. O. . |
| WO89/05123 | 6/1989 | World Int. Prop. O. . |
| 89/07419 | 8/1989 | World Int. Prop. O. . |
| WO90/07303 | 7/1990 | World Int. Prop. O. . |
| WO91/14401 | 10/1991 | World Int. Prop. O. . |

OTHER PUBLICATIONS

Circulation, vol. 81, No. 2, 2/190, "Application of a New Phased-Arrayed Ultrasound Imaging Catheter in the Assessment of Vascular Dimensions", pp. 660–666.

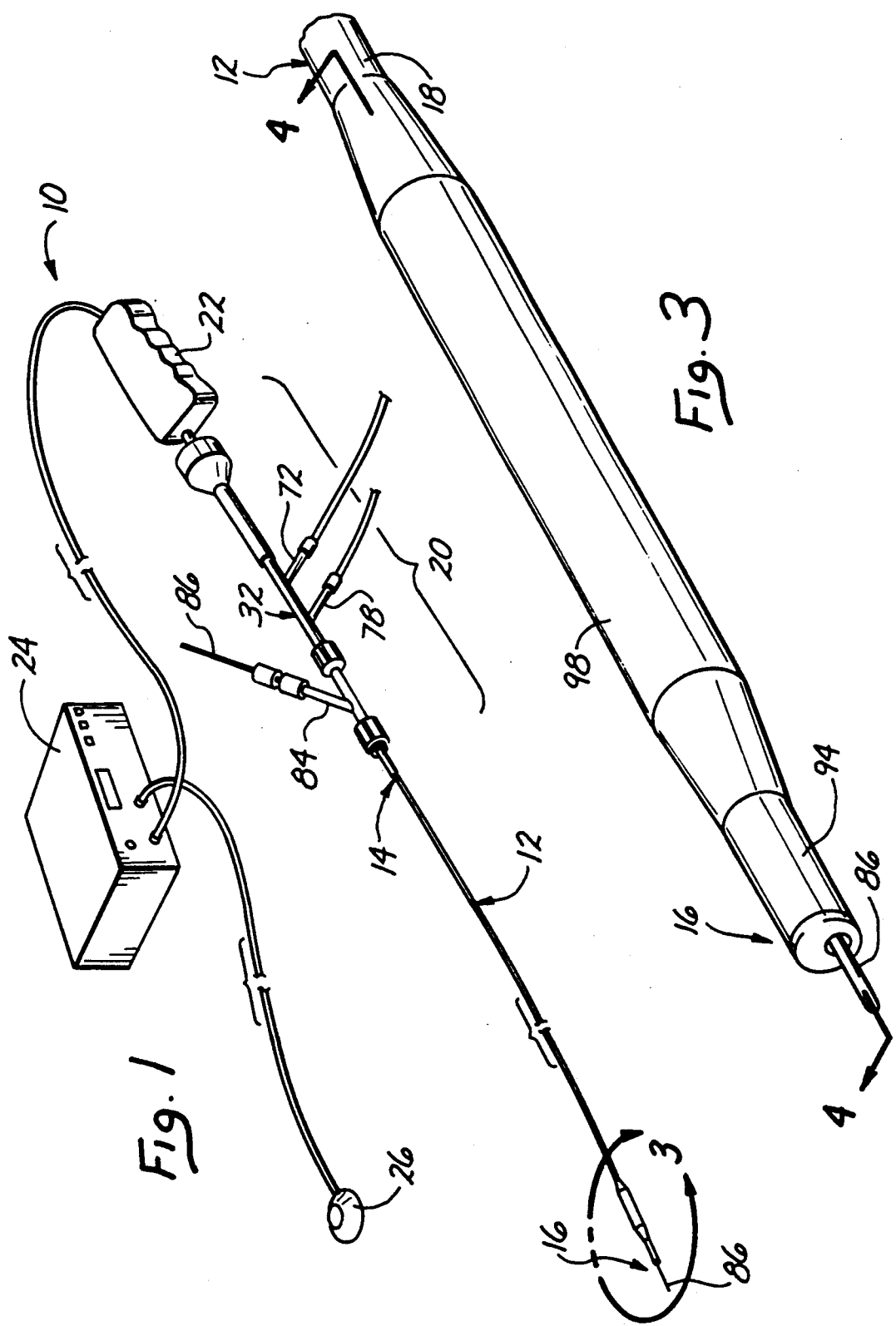

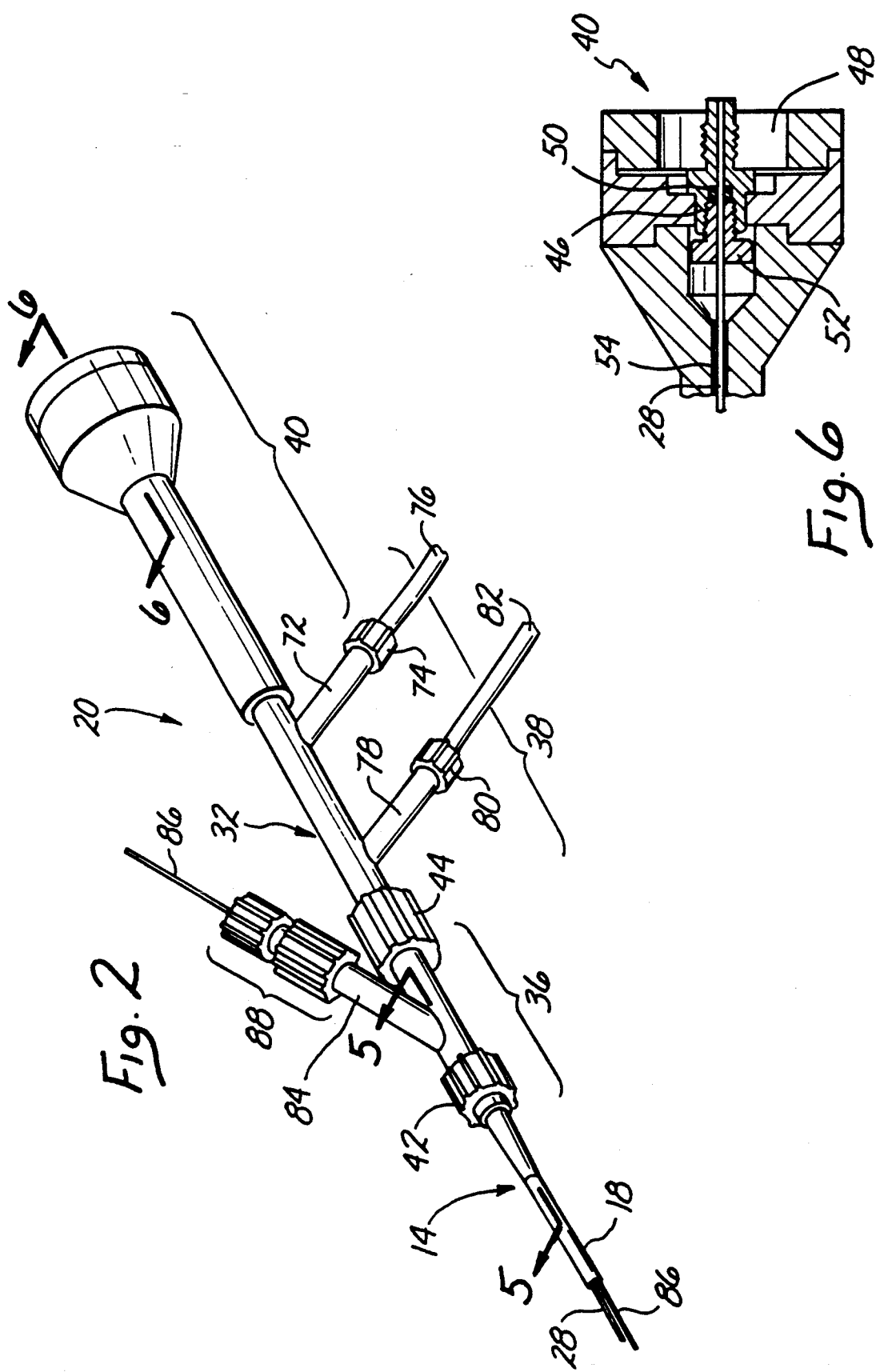

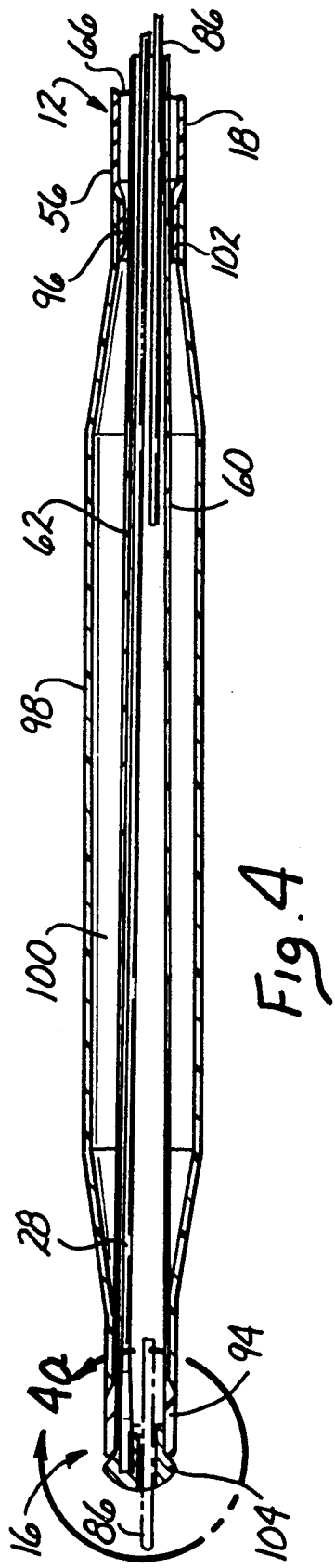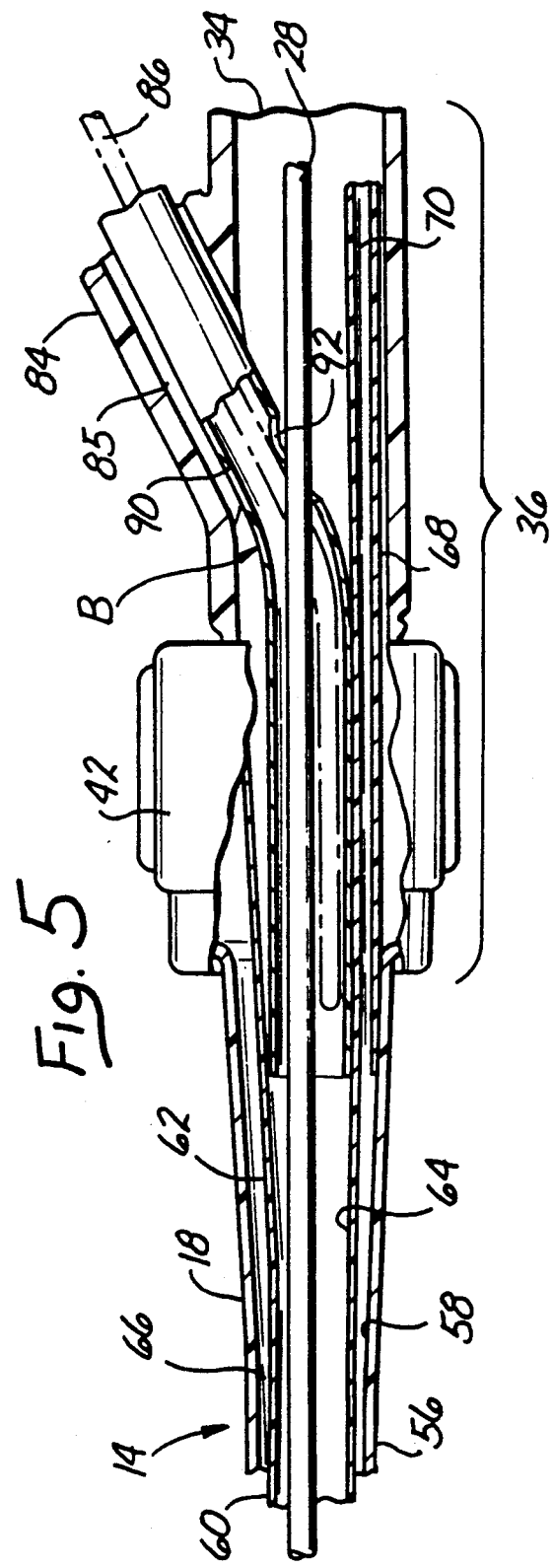

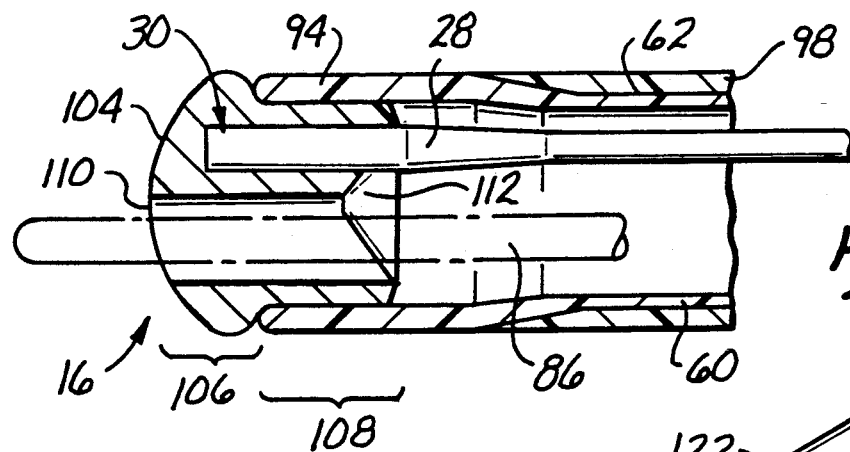
Fig 4a
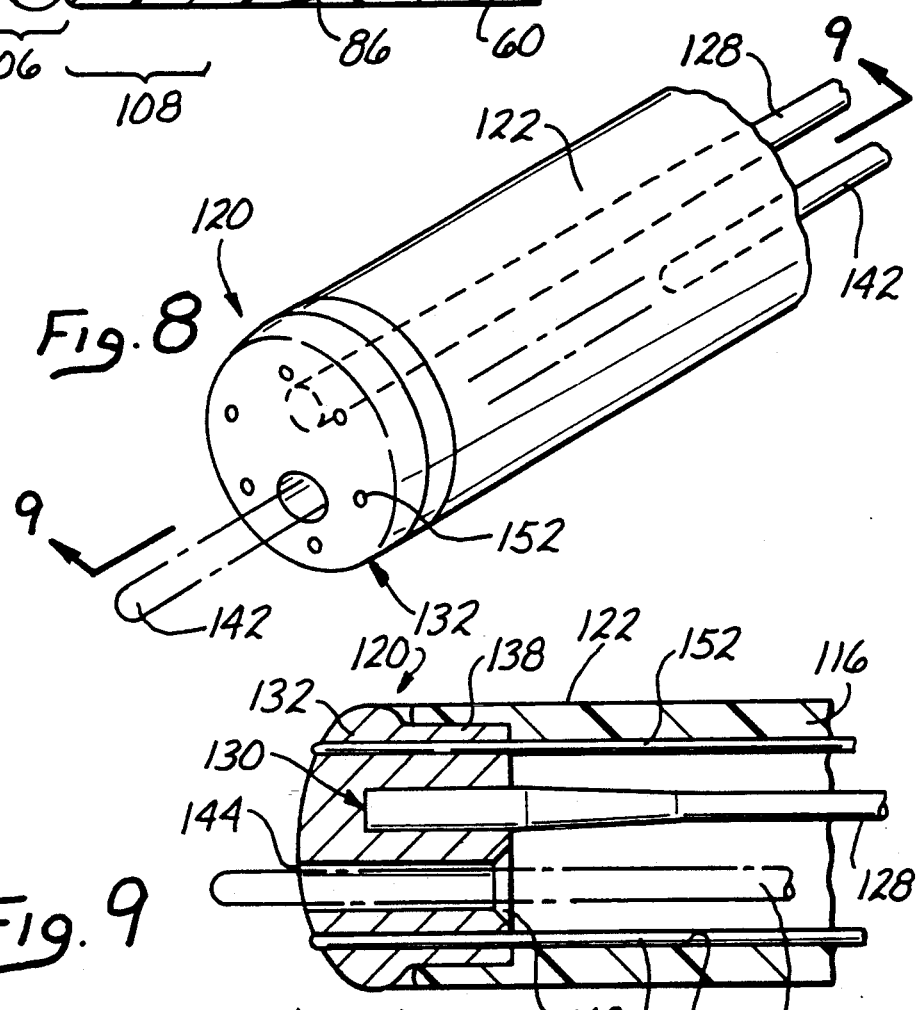
Fig. 8
Fig. 9
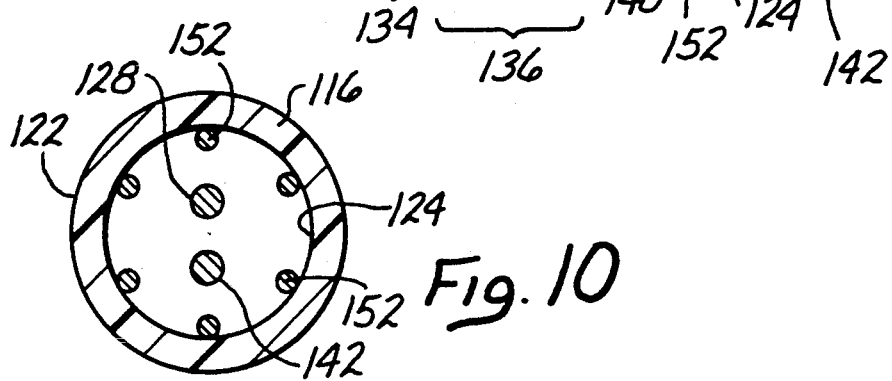
Fig. 10

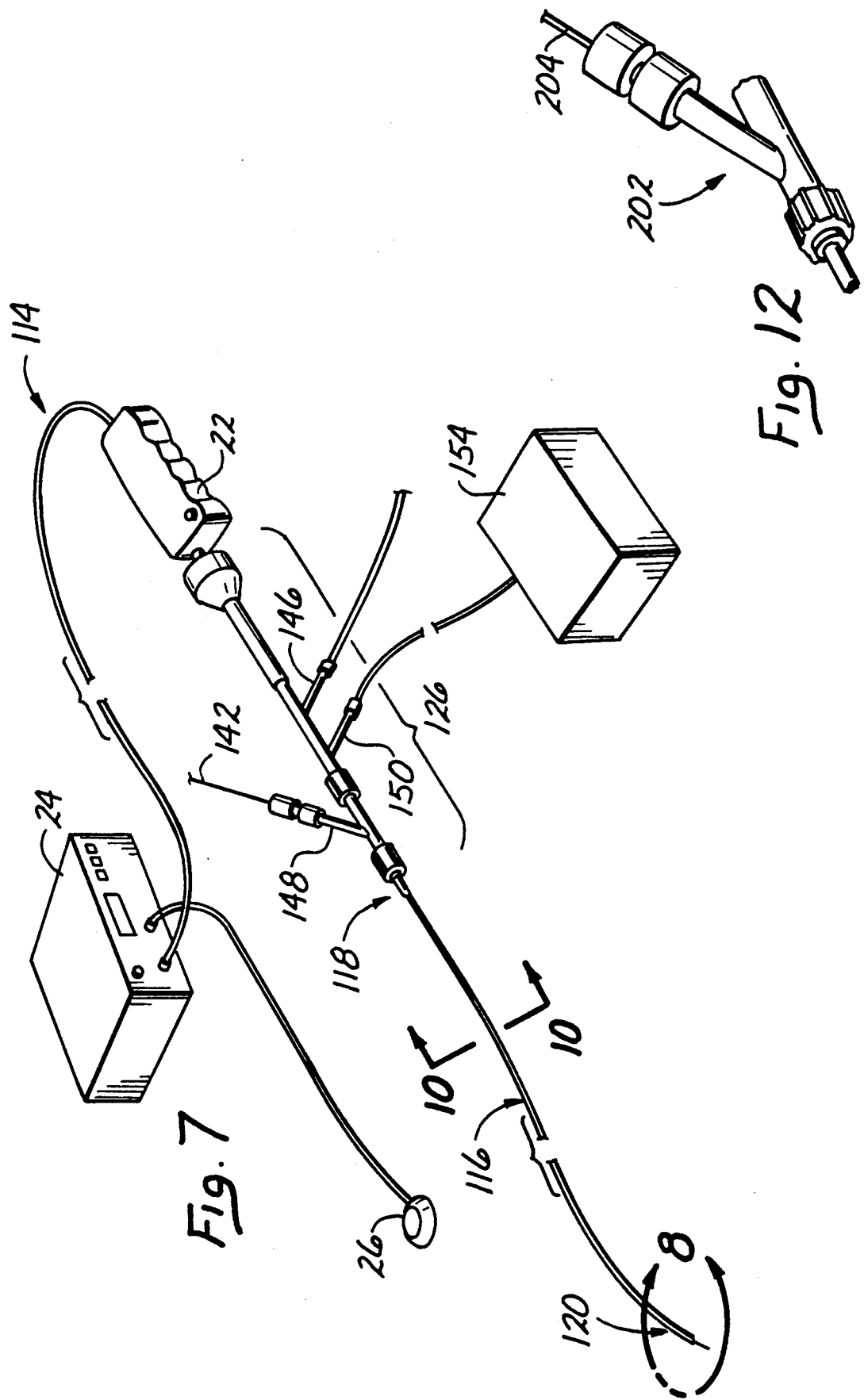

ANGIOPLASTY AND ABLATIVE DEVICES HAVING ONBOARD ULTRASOUND COMPONENTS AND DEVICES AND METHODS FOR UTILIZING ULTRASOUND TO TREAT OR PREVENT VASOPASM

RELATED APPLICATION

This patent application is a continuation-in-part of U.S. patent application Ser. No. 640,190 filed Jan. 1, 1991 entitled ULTRASOUND ANGIOPLASTY DEVICE INCORPORATING IMPROVED TRANSMISSION MEMBER AND ABLATION PROBE, and U.S. patent application Ser. No. 878,795 filed May 5, 1992 entitled MODIFIED ULTRASONIC CATHETER U.S. Pat. No. 5,267,954, the entire disclosures of both such prior patent applications being hereby expressly incorporated herein by reference.

FIELD OF THE INVENTION

The present invention relates generally to medical devices and more particularly to devices and methodology for treating occlusive vascular disorders and for preventing untoward side effects associated with such treatment.

BACKGROUND OF THE INVENTION

A number of devices have heretofore been utilized for removal, dilation or ablation of occlusive matter from the lumens of blood vessels.

Examples of the types of devices which have heretofore been utilized to dilate, ablate or otherwise remove obstructions from blood vessels include a.) balloon angioplasty catheters which function to radially dilate an occlusive lesion, b.) ultrasound ablation catheters which serve to ultrasonically ablate the occlusive lesion, c.) laser catheters which vaporize or ablate the occlusive lesion by laser energy and d.) atherectomy devices which operate to cut, shave, or grind occlusive matter from the blood vesel lumen using mechanical means.

Examples of ultrasonic ablation devices are described in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,B70,953 (Don Michael, et al.), 5,069,664 (Suess, et al.) and 4,920,954 (Alliger, et al.), as well as other patent publications W087-05739 (Cooper), W089-06515 (Bernstein, et al.), W090-0130 (Sonic Needle Corp.), EP316789 (Don Michael, et al.), DE 3,821,836 (Schubert), DE2438648 (Pohlman), and EP 0443256A1 (Baruch).

Examples of atherectomy devices include those described in U.S. Pat. No. 5,100,423 (Fearnot) and EP0347098A2 (Shiber).

Although laser ablation, ultrasonic ablation and atherectomy devices have been utilized for ablating or removing occlusive matter from blood vessels, balloon dilation angioplasty remains the most widely utilized interventional technique for nonsurgical restoration of patency in occluded or partially occluded blood vessels. One problem associated with balloon dilation angioplasty is that, in blood vessels which are fully occluded, it is sometimes difficult to penetrate the occlusive matter in a manner which permits the dilation balloon to become operatively positioned adjacent the occlusive lesion. In view of this problem, there exists a need in the art for development of a balloon dilation catheter having an onboard ablation component for partially ablating, or opening a channel through the offending lesion, thereby facilitating operative advancement and positioning of the dilation balloon within the offending lesion.

Another problem associated with balloon dilation angioplasty as well as other intravascular ablation or surgical procedures (e.g. laser ablation or atherectomy) is the occurrence of constrictive vasospasm in the affected blood vessel during or immediately after the procedure. Severe vasospasm may result in complete occlusion of the affected blood vessel, thereby presenting an acute clinical emergency.

The occurrence of vasospasm can result in ischemia or infarction and, at last theoretically, may promote intravascular thrombus formation. See, Fischell, T. A., Derby, G., Tse, T. M. and Stadius, M. L.; Coronary Artery Vasoconstriction Routinely Occurs After Percutaneous Transluminal Coronary Angioplasty: A Quantitative Arteriographic Analysis; Circulation; Vol 78; 1323-1334 (1988). One means of treating vasospasm is to administer vasorelaxant pharmacologic agents to prevent or relieve the untoward vasospasm. Recent observations have indicated that the administration of ultrasonic energy to the blood vessel, in the region of the vasospasm, may effect rapid vasorelaxation without the need for administration of pharmacological agents. (Abstract) Chokahi, S. K., et al. ULTRASONIC ENERGY PRODUCES ENDOTHELIUM-DEPENDENT VASOMOTOR RELAXATION IN VITRO, Abstracts of the 62nd Scientific Sessions of the American Heart Association (1989). Accordingly, it is desirable to develop ultrasonic devices and methods for preventing or treating vasospasm angioplasty or ablative procedures.

SUMMARY OF THE INVENTION

The present invention includes a combination balloon dilation/ultrasound ablation catheter device. The combination balloon dilation/ultrasound ablation device of the present invention comprises an elongate intravascular catheter having at least one dilation balloon formed thereon for radially or otherwise dilating an occlusive lesion. Additionally, an elongate ultrasound transmission member or waveguide extends longitudinally through the body of the catheter. The proximal end of the ultrasound transmission member or waveguide is connectable to an ultrasound generating device, such as an ultrasound transducer. The distal end of the ultrasound transmission member or waveguide is positioned adjacent, flush with, or near the distal end of the catheter body and may be securely attached or anchored thereto. When it is desired to advance the distal end of the catheter body into a body of occlusive material or high grade stenosis, the ultrasound transmitting device may be operated to pass ultrasonic energy through the ultrasound transmission member or waveguide at a wavelength and power sufficient to effect ultrasonic ablation of at least a portion of the occlusive matter, so as to form a pilot hole or passageway therethrough. Thereafter, the catheter may be further advanced distally to a point where the dilation balloon is positioned within or adjacent the remainder of the obstructive matter. The dilation balloon may then be operated in accordance with standard balloon dilation angioplasty principles to effect radial or other dilation of the occlusive matter. Additionally, the presence of the ultrasound component within the ultrasound ablation/balloon dilation catheter device provides a means for delivering ultrasound energy to prevent or treat vasospasm.

Additionally, the present invention includes methods and devices for preventing or treating vasospasm in tubular anatomical structures such as blood vessels during various intravascular, diagnostic or interventional procedures. Ultrasonic energy at a wavelength of approximately 20 Khz is preferable for preventing or treating vasospasm. The ultrasound for preventing or treating vasospasm may be delivered through an onboard ultrasound transmission component positioned within a standard diagnostic or interventional catheter such as a balloon dilation angioplasty catheter, laser ablation catheter or atherectomy catheter device. Alternatively, if such devices are devoid of an onboard ultrasound transmitting component, a separate ultrasound transmission wire or waveguide may be rapidly inserted through the working lumen or guidewire lumen of a standard catheter or other intravascular device so as to prevent or treat vasospasm by delivery of ultrasonic energy at or near the distal end of the catheter or device.

Further and more specific aspects of the present invention Will become apparent to those skilled in the art upon reading and understanding the following detailed description of preferred embodiments, and the accompanying drawings.

BRIEF DESCRIPTION OF THE DRAWINGS

These as well as features of the present invention will become more apparent upon reference to the drawings wherein:

FIG. 1 is a perspective view of a catheter device of a first embodiment of the present invention incorporating both ultrasound ablation and balloon dilation components;

FIG. 2 is an enlarged perspective view of a proximal end connector assembly positionable on the proximal end of the ultrasound/balloon catheter body shown in FIG. 1;

FIG. 3 is an enlarged perspective view of the distal end of the ultrasound/balloon catheter body designated by the numeral 3 in FIG. 1;

FIG. 4 is a cross-sectional view taken along line 4—4 of FIG. 3;

FIG. 4a is an enlarged cross-sectional view of the distal end of the ultrasound/balloon catheter body designated by the numeral 4a in FIG. 4;

FIG. 5 is a cross-sectional view taken along line 5—5 of FIG. 2;

FIG. 6 is a cross-sectional view taken along line 6—6 of FIG. 2;

FIG. 7 is a perspective view of a laser ablation catheter equipped with an ultrasound component for delivering vasorelaxant ultrasound energy during a laser ablation procedure;

FIG. 8 is an enlarged perspective view of the distal portion of the laser catheter body designated by the numeral 8 in FIG. 7;

FIG. 9 is a cross-sectional view taken along line 9—9 of FIG. 8;

FIG. 10 is a cross-sectional view taken along line 10—10 of FIG. 7;

FIG. 12 is a perspective view of a conventional proximal end connector assembly for use with the insertable ultrasonic device shown in FIG. 11;

DETAILED DESCRIPTION OF THE PREFERRED EMBODIMENTS

Figure 11:
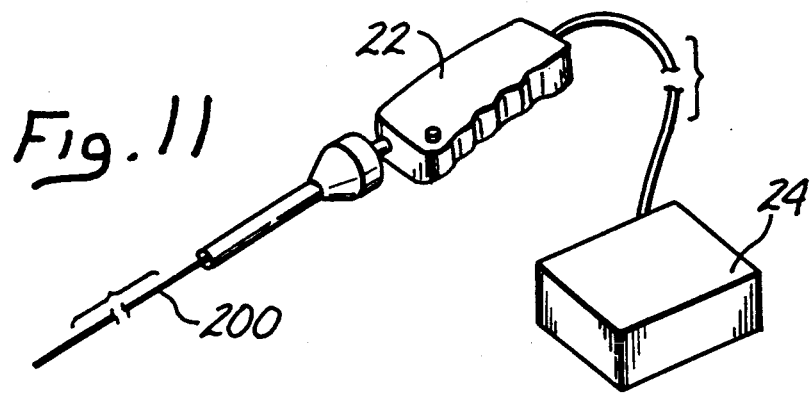
FIG. 11 is a perspective view of an insertable ultrasound device which is insertable through a working lumen of a catheter to effect ultrasonic treatment of vasospasm.

The detailed description set forth below in connection with the appended drawings is intended merely as a description of the presently preferred embodiments of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments that are also intended to be encompassed within the spirit and scope of the invention.

i. A Preferred Ultrasound Ablation/Balloon Dilaton Catheter

FIG. 1 is a perspective showing of an ultrasonic ablation/balloon dilation catheter device 10 constructed in accordance with a first embodiment of the present invention which incorporates combined ultrasound ablation and balloon dilation components. In the first embodiment, the catheter device 10 comprises an elongate catheter body 12 having a proximal end 14, a distal end 16 and defining an outer surface 18. Mounted on the proximal end 14 of the catheter body 12 is a proximal end connector assembly 20. An ultrasound transducer 22 is connected to the proximal end of the connector assembly 20. An ultrasound generator 24 having a foot actuated on/off switch 26 is operatively connected to the ultrasound transducer 22 so as to send ultrasonic energy through the catheter body 12 via an ultrasound transmission member 28 or waveguide Which extends longitudinally through the catheter body 12. The ultrasound transmission member 28 or waveguide has a proximal end which is connectable to the ultrasound transducer 22 such that the ultrasonic energy will pass through the ultrasound transmission member 28 to the distal end 30 thereof and, hence, the distal end 16 of the catheter body 12.

In the first embodiment, the ultrasound transmission member 28 may be formed of any material capable of effectively transmitting the ultrasonic energy from the ultrasound transducer 22 to the distal end 16 of the catheter body 12, including but not necessarily limited to metal, plastic, hard rubber, ceramic, and/or composites thereof. In accordance with one aspect of the invention, all or a portion of the ultrasound transmission member 28 may be formed of one or more materials which exhibit super-elasticity. Such materials should preferably exhibit super-elasticity consistently within the range of temperatures normally encountered by the ultrasound transmission member 28 during operation of the catheter device 10. Specifically, all or part of the ultrasound transmission member 28 may be formed of one or more metal alloys known as "shape memory alloys".

Examples of super-elastic metal alloys which are usable to form the ultrasound transmission member 28 of the present invention are described in detail in U.S. Pat. Nos. 4,665,906 (Jervis); 4,565,589 (Harrison); 4,505,767 (Quin); and 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries, and behavior of specific metal alloys which are super-elastic within the temperature range at which the ultrasound transmission member 28 of the present invention operates, any and all of which super-elastic metal alloys may be usable to form the super-elastic ultrasound transmission member 28.

In particular, one presently preferred super-elastic metal alloy of which the ultrasound transmission member 28 may be formed is a nickel-titanium alloy wire made up of 55.8 weight percent nickel (NiTi containing 55.8% weight % Ni balance Ti). Such material is commercially available as Tinel ™ Wire from Raychem Corporation, Menlo Park, Calif. As will be recognized, in any embodiment of the present invention, the ultrasound transmission member 28 may be tapered, narrowed, or otherwise reduced in cross-sectional dimension within the catheter device 10 so as to decrease the rigidity of the ultrasound transmission member 28 and/or to cause amplification of the ultrasound transmitted to and from the distal end 30 thereof.

Referring now to FIGS. 2 and 5, the proximal end connector assembly 20 comprises an elongate, rigid body 32 having a hollow bore 34 extending longitudinally therethrough. In the embodiment shown, the elongate body 32 of the proximal end connector assembly 20 is actually constructed of a frontal portion 36, a mid-portion 38 and a rear portion 40. The frontal portion 36 of the elongate body 32 is firmly connected to the proximal end 14 of the catheter body 12 by way of a threaded gripping member 42 engaged thereto. As will hereinafter be more fully described, the proximal end 14 of the catheter body 12 has a flared configuration and includes an annular flange formed on the outermost end thereof which is brought into sealed engagement with the connector assembly 20 when the gripping member 42 is threadably engaged to the body 32. The proximal end of the frontal portion 36 is connected to the distal end of the mid-portion 38 of the elongate body 32 by way of a second gripping member 44. As will be recognized, to facilitate the aforementioned construction, threads are formed on the opposite ends of the frontal portion 36 of the elongate body 32. Threads are also formed on the proximal end of the mid-portion 38 of the elongate body 32 such that the mid-portion 38 may be threadably received into a correspondingly threaded bore formed in the distal end of the rear portion 40 of the elongate body 32.

Referring now to FIG. 6, the ultrasound transmission member 28 or waveguide extends longitudinally through the entire catheter body 12 and through the proximal end connector assembly 20. The ultrasound transmission member 28 is inserted into and engaged by a threaded proximal connector 46. Threaded proximal connector 46 is positioned within a cylindrical recess 48 formed in the proximal end of the connector assembly 20. The ultrasound transducer 22 may be screwed onto and threadably connected to the proximal connector 46 to accomplish passage of ultrasonic energy through the ultrasound transmission member 28 in a distal direction to the distal end 16 of the catheter body 12.

The extreme proximal end of the connector assembly 20 is provided with a sonic connector assembly or apparatus configured to effect operative attachment of the proximal end of the ultrasound transmission member 28 to the horn of the ultrasound transducer 22. The sonic connector assembly or apparatus is preferably configured and constructed to permit passage of ultrasound energy through the ultrasound transmission member 28 with minimal lateral side-to-side movement of the ultrasound transmission member 28 while, at the same time, permitting unrestricted longitudinal forward/backward vibration or movement of the ultrasound transmission member 28. Specifically, a distal portion of the body of the threaded proximal connector 46 is configured to receive therein a compressible gripping ferrule 50. Compressible gripping ferrule 50 has a small central aperture formed therethrough through which the ultrasound transmission member 28 passes, as shown. A frontal member 52 is threadably tightened within the frontal portion of the body of the proximal connector 46 so as to compress gripping ferrule 50, thereby causing gripping ferrule 50 to firmly grip and hold the ultrasound transmission member 28 in place within the body of the proximal connector 46. The proximal connector 46 may then be compressed or crimped inwardly so as to be additionally crimp connected or crimp fit to the proximal end of the ultrasound transmission member 28, thereby providing further gripping and attachment of the sonic connector assembly to the proximal end of the ultrasound transmission member 28. A series of threads are formed on the outer surface of the proximal connector 46 to permit the distal end of the ultrasound transducer horn to be threadably screwed onto and releasably attached to the sonic connector assembly. Thus, the frontal member 52, gripping ferrule 50, and proximal connector 46 combine to form a sonic connector assembly to which the horn of the ultrasound transducer 22 may be attached and through which the ultrasonic energy may be transmitted into the ultrasound transmission member 28. A lumen 54 extending through the rear portion 40 of the connector assembly 20 is specifically sized to be large enough to permit the ultrasound transmission member 28 to pass therethrough with a small amount of space remaining between the outer surface of the ultrasound transmission member 28 an the inner luminal surface of the lumen 54.

Referring now to FIG. 5, in the first embodiment the catheter body 12 is formed of two concentric single lumen tubes. Particularly, the catheter body 12 comprises a first outer tube 56 which defines the outer surface 18 of the catheter body 12 and further defines a first inner luminal surface 58. Longitudinally disposed through and within the lumen of the first outer tube 56 is a second inner tube 60 defining a second outer surface 62 and a second inner luminal surface 64. As seen in FIG. 5, the previously described annular flange formed about the proximal end 14 of the catheter body 12 is actually formed about the proximal end of the outer tube 56 and engaged to the connector assembly 12 via the gripping member 42. In the first embodiment, outer tube 56 and inner tube 60 are preferably sized such that when the inner tube 60 is longitudinally disposed within the outer tube 56, space 66 is defined between the second outer surface 62 of the inner tube 60 and the first inner luminal surface 58 of the outer tube 56.

Attached to a portion of the first inner luminal surface 58 adjacent the proximal end of the outer tube 56 is a wall member 68 which extends toward the proximal end of the connector assembly 20. Wall member 68 is preferably attached to the first inner luminal surface 58 via a heat sealing process, though an adhesive or other attachment method may be utilized as an alternative. As further seen in FIG. 5, the proximal ed of the inner tube 60 is formed in a manner wherein a proximal portion thereof extends toward the proximal end of the connector assembly 20. Advantageously, when the proximal end of the inner tube 60 is engaged to the gripping member 42, the portion thereof extending toward the proximal end of the connector assembly is interfaced to the wall member 68 in a manner forming a balloon inflation lumen 70 which is in fluid communication with the space 66 defined between the inner tube 60 and outer tube 56. In this respect, the proximal end of the inner tube 60 is engaged to the connector assembly 20 in a manner wherein the only access into the space 66 is via the balloon inflation lumen 70. In the first embodiment, the space 66 comprises part of the balloon inflation lumen 70 due to its fluid communication therewith. It will be recognized that as an alternative to forming the balloon inflation lumen 70 from the wall member 68 and a portion of the inner tube 60, such lumen may be formed from a separate tubular member which is fluidly connected to the proximal end of the inner tube 60 in a manner wherein the space 66 is accessible only thereby. The use of the balloon inflation lumen 70 in conjunction with the space 66 will hereinafter be discussed.

Formed on and extending outwardly from the body 32 in the mid-portion 38 of the connector assembly 20 is a first fluid inlet sidearm or irrigation port 72. Extending through the irrigation port 72 is a hollow bore which is in fluid communication with the bore 34 of the connector assembly 20. Threadably engaged to the outermost end of the irrigation port 72 is a connector member 74 which is used to threadably connect the irrigation port 72 to an irrigation fluid supply source 76. Also formed on the body 32 and extending outwardly from the mid-portion 38 of the connector assembly 20 is a balloon inflation port 78. Like the irrigation port 72, balloon inflation port 78 includes a hollow bore which extends therethrough and is in fluid communication with the balloon inflation lumen 70 and, hence, the space 66. Attached to the outermost end of balloon inflation port 78 is a connector member 80 which is used to threadably engage the balloon inflation port 78 to a balloon inflation fluid supply source 82.

As best seen in FIG. 5, the ultrasound transmission member 28 extends through the bore 34 of the connector assembly 20 and is subsequently received into the lumen of the inner tube 60. Due to the fluid communication between the irrigation port 72 and the bore 34, pressurized fluid such as a coolant liquid may be infused through irrigation port 72, bore 34, and through the lumen of the inner tube 60. Such liquid will flow out the distal end 16 of the catheter body 12 in a manner which will hereinafter be described. The temperature and flow rate of such coolant liquid may be specifically controlled to maintain the temperature of the ultrasound transmission member 28 at a desired temperature within its optimal Working range. In particular, in embodiments of the invention wherein the ultrasound transmission member 28 is formed of a metal alloy which exhibits optimal physical properties (e.g. super elasticity) within a specific range of temperatures, the temperature and flow rate of coolant liquid infused through the irrigation port 72 may be specifically controlled to maintain the temperature of the ultrasound transmission member 28 within the range of temperatures at which it demonstrates its most desirable physical properties. For example, in embodiments of the invention wherein the ultrasound transmission member 28 is formed of a shape memory alloy which exhibits super elasticity when in its martensite state, but which loses super elasticity as it transitions to an austenite state, it will be desirable to adjust the temperature and flow rate of the coolant infused through the irrigation port 72 so as to maintain the shape memory alloy of the ultrasound transmission member 28 within a temperature range at which the alloy will remain in its martensite state and will not transition to an austenite state. The temperature at which such shape memory alloys transition from a martensite state to an austenite state is known as the "martensite transition temperature" (Ms) of the material. Thus, in these embodiments, the fluid infused through irrigation port 72 will be at such temperature, and will be infused at such rate, as to maintain the shape memory alloy of the ultrasound transmission member 28 below its martensite transition temperature (Ms).

Formed on the body 32 and extending outwardly from the frontal portion 36 of the connector assembly 20 is a guidewire insertion sidearm 84 for receiving a transluminal body guidewire 86. The guidewire insertion arm 84 includes a hollow bore extending therethrough which communicates with the bore 34 of the connector assembly 20. A guidewire gripping/sealing apparatus 88 may be mounted on guidewire insertion arm 84 to grasp and hold the guidewire 86 in fixed longitudinal position relative to the catheter device 10 and to provide a seal to prevent backflow of blood through the catheter device 10. Examples of guidewire gripping/sealing apparatus 88 which may be utilized in this application include those which are available commercially as Product Nos. 1905017A and 1905014A from Medical Disposables International, West Conshocken, Pa.

In the embodiment of the connector assembly 20 shown in FIG. 5, an angled guidewire diverter tube 90 is positioned within the bore 85 of guidewire insertion arm 84 and a portion of the longitudinal bore 34 of the body 32 of the connector assembly 20. Additionally, the distal end of the diverter tube 90 extends through the bore 34 and into the proximal end of the inner tube 60. The guidewire diverter tube 90 comprises an obtuse angular bend B having an aperture 92 formed at the outer apex of such angular bend B. The aperture 92 is sufficiently large to permit the ultrasound transmission member 28 to pass longitudinally therethrough without damping or interference from the body of the diverter tube 90. Also, the aperture 92 is sufficiently large to allow irrigation/coolant liquid to flow from the bore 34 therethrough when the ultrasound transmission member 28 is positioned within the aperture 92. As will hereinafter be discussed, the guidewire 86 is inserted into the distal end 16 of the catheter body 12 and into the lumen of the inner tube 60. As such, the diverter tube 90 is configured and constructed such that, as the proximal end of the guidewire 86 is advanced in a proximal direction through the lumen of the inner tube 60, it will impinge against the wall of the diverter tube 90 and will thus be diverted outwardly through the guidewire insertion arm 84.

Referring now to FIGS. 3, 4, and 4a, as previously specified, the catheter body 12 of the catheter device 10 comprises the outer tube 56 having the inner tube 60 disposed longitudinally therein. The guidewire 86 extends longitudinally through the lumen of the inner tube 60 as does the ultrasound transmission member 28. In the first embodiment, the catheter body 12, and more particularly the outer tube 56, has an outside diameter of 0.5 mm–5.0 mm. However, if the catheter body 12 is intended for insertion into tortuous or relatively small anatomical structures (e.g., the coronary arteries), it is preferable that the outer diameter of the outer tube 56 be 0.25 mm–2.5 mm.

As seen in FIG. 4, the inner tube 60 is sized to extend axially beyond the distal end of the outer tube 56 and is formed to include an enlarged annular head portion 94 about the distal end thereof. Additionally, formed about the distal end of the outer tube 56 is an annular recessed portion 96. Attached to the distal end 16 of the catheter body 12 is a dilation balloon 98 having a proximal end attached to the outer tube 56 by an overlapping joint (OJ) and a distal end of attached to the inner tube 60. Particularly, the proximal end of the dilation balloon 98 is nested into the annular recessed portion 96 and sealed thereagainst with the proximal end being abutted against the head portion 94 and sealed against a portion of the outer surface 62 of the inner tube 60. Advantageously, due to the configuration of the head portion 94 and recessed portion 96, the proximal end of the balloon 98 forms a continuous surface with the outer tube 56 when sealed thereto with the distal end forming a continuous surface with the head portion 94 of the inner tube 60 when sealed to the outer surface 62 of the inner tube 60. The balloon 98 is preferably sealed to the outer tube 56 at overlapping joint (OJ) and to the distal portion of inner tube 60 by a heat sealing process, though adhesives or other suitable affixation apparatus, substances or methods may also be utilized.

As shown in FIG. 4, the distal most portion of inner tube 60 is enlarged or outwardly tapered such that the distal end of inner tube 60 is of greater diameter than that portion of inner tube 60 which resides adjacent the overlapping joint (OJ) between outer tube 56 and balloon member 98. Such tapering of the inner tube 60 prevents or minimizes interference with or contact between the inner tube 60 and the recessed portion 96 of outer tube 56 at overlapping junction (OJ). Additionally, such minimization of the diameter of a portion of the inner tube 60 further enables the deflated balloon 98 to assume a substantially flat non-prodrudding configuration consistent with the remainder of the outer surface of the catheter body 12. In this regard, the balloon member 98 may be specifically shaped such that its diameter tapers inwardly or narrows from its proximal end to its distal end in porportion to the corresponding widening or enlargement of the inner tube 60, thereby ensuring a completely flat non-protrudding configuration when the balloon member 98 is deflated and collapsed against the outer surface of inner tube 60.

As also seen in FIG. 4, when the dilation balloon 98 is attached to the outer tube 56 and inner tube 60 in the aforementioned manner, an inflation space 100 is defined between the dilation balloon 98 and outer surface 62 of the inner tube 60. In the first embodiment, the inflation space 100 is placed in fluid communication with the space 66 via an annular passage 102 defined by the recessed portion 96 of the outer tube 56. As previously specified, the space 66 is in fluid communication with and forms part of the balloon inflation lumen 70 which is itself fluidly connected to the inflation fluid supply source 82 via the inflation port 78. As such, the balloon inflation fluid introduced into the inflation port 78 flows through the inflation lumen 70, space 66, and annular passage 102 into the inflation space 100 in a manner operable to selectively dilate or deflate the balloon 98. In the first embodiment, the dilation balloon 98 is approximately 5 millimeters in length and is positioned on the catheter body 12 such that the distal-most extent of the dilation balloon 98 is approximately 3 millimeters from the distal end 16 of the catheter body 12, and more particularly, the distal-most extent of the head portion 94 of the inner tube 60.

As best seen FIG. 4a, the distal end 30 of the ultrasound transmission member 28 has an enlarged configuration. Mounted on the enlarged distal end 30 of the ultrasound transmission member 28 is a distal head 104. In the embodiment shown, the distal head 104 comprises a generally round, conical, or disk-shaped distal portion 106 and a reduced diameter neck or proximal portion 108. The outer diameter of the proximal portion 108 of the distal head 104 is approximately the same as or slightly less than the inner diameter of the lumen of the inner tube 60 such that the proximal portion 108 of the distal head 104 may be inserted into the distal end of the lumen of the inner tube 60 to a point where the distal-most end of the head portion 94 abuts against the proximal aspect of the distal portion 106 of the distal head 104, as shown. The distal head 104 is firmly bonded, attached, or connected to the catheter body 12, and more particularly the inner tube 60, such that the distal head 104 is prevented from undergoing longitudinal or transverse movements separate from or relative to the catheter body 12. Such non-movable affixation of the distal head 104 to the inner tube 60 prevents longitudinal or transverse movement of the distal head 104 apart from the catheter body 12. Additionally, such affixation of the distal head 104 to the inner tube 60 increases the conveyance of ultrasound energy into the distal end 16 of the catheter body 12, thereby resulting in enhanced cavitation effects created by the distal end 16 of the catheter body 12. Such bonding connection or attachment of the distal head 104 to the inner tube 60 of the catheter body 12 may be accomplished by any suitable means. One means of attaching the distal head 104 to the inner tube 60 is through the use of an adhesive which is applied to the proximal portion 108 of the distal head 104 prior to insertion thereof into the distal end of the inner tube 60. The adhesive may comprise any suitable adhesive, such as cyanoacrylate (e.g., Loctite TM, Loctite Corp., Ontario, Canada or Aron Alpha TM, Borden, Inc., Columbus, Ohio) or polyurethane (e.g., Dymax TM, Dymax Engineering Adhesive, Torrington, Conn.) to firmly bond and attach the distal head 104 to the inner tube 60. The distal head 104 may be formed of any suitable rigid material, such as metal or plastic. In devices wherein the distal head 104 is formed of plastic, the surrounding inner tube 60 may be thoroughly welded, heat sealed, or solvent welded to the plastic distal head 104, in accordance with the types of plastics employed.

In the alternative to the use of adhesives, various mechanical or frictional connectors, such as screw threads, lugs, or other surface modifications formed on the proximal portion 108 of the distal head 104, may be utilized to hold the distal head 104 in a fixed position relative to the inner tube 60 of the catheter body 12. In such embodiments, corresponding grooves, detents, or surface modifications may also be formed in the surrounding inner luminal surface 64 of the inner tube 60 so as to cooperate with any such threads, lugs, or other surface modifications formed on the opposing surface of the distal head 104. Such threads, lugs, or other surface modifications will be configured and constructed as to mechanically or frictionally hold the distal head 104 in fixed position relative to the catheter body 12.

The distal head 104 is preferably formed of radiodense material so as to be easily discernible by radiographic means. Accordingly, the distal head 104 may preferably be formed of metal or, alternatively, may be formed of plastic, ceramic, or rubber materials, optionally having one or more radiodense markers affixed thereto or formed therein. For example, the distal head 104 may be molded of plastic, such as acrylonitrile-butadiene-styrene (ABS) and one or more metallic foil strips or other radiopaque markers may be affixed to such plastic distal head 104 in order to impart sufficient radiodensity to permit the distal head 104 to be readily located by radiographic means. Additionally, in embodiments wherein the distal 104 is formed of molded plastic or other non-metallic material, a quantity of radiodense fillers, such as powdered Bismuth or Barium Sulfate (BaSo), may be disposed within the plastic or other non-metallic material of which the distal head 104 is formed so as to impart enhanced radiodensity thereto.

Extending longitudinally through the distal head 104 is a guidewire passage aperture 110. The guidewire passage aperture 110 is preferably formed through the distal head 104 at a location wherein the guidewire 86 may pass therethrough into the lumen of the inner tube 60. The guidewire passage aperture 110 may be sized so as to be slightly larger than the outer diameter of the guidewire 86 to be passed therethrough so as to permit fluid to be infused through the lumen of the inner tube 60 and pass out of the guidewire passage aperture 110, even when the guidewire 86 is extending therethrough. The distal head 104 further includes a conical depression 112 disposed in the proximal portion 108 thereof to direct the guidewire 86 into the guidewire passage aperture 110.

As an alternative to the utilization of the distal head 104, the distal end 30 of the ultrasound transmission member 28 may be directly affixed to the distal end of the catheter body 12, and more particularly to a distal portion of the inner luminal surface 64 of the inner tube 60. Additionally, the distal head 104 mounted to the distal end 30 of the ultrasound transmission member 28 may be unaffixed to the inner tube 60 of the catheter body 12.

The combination ultrasound ablation/balloon dilation catheter device 10 of the present invention is particularly suited for treating total occlusions and high grade stenoses of blood vessels, wherein it is difficult to initially advance the dilation balloon 98 due to the degree of vessel occlusion. In such cases, the ultrasound ablation component of the device may be utilized to form a pilot hole or passageway through the occlusion or high grade stenosis, thereby enabling the distal portion of the catheter 12 to be advanced into the occlusion or stenosis such that the deflated balloon 98 will be operatively positioned adjacent thereto. Thereafter, the balloon 98 may be repeatedly inflated and deflated, in accordance With standard balloon dilation angioplasty techniques, to effect dilation of the remainder of the occlusion or stenosis.

If vasoconstriction or vascular spasm occurs before, during or after the balloon dilation by balloon 98, the ultrasound component of the device 10 may be utilized to treat or reverse such vasoconstriction or spasm. This is accomplished by utilizing the signal generation device 24 and ultrasound transducer 22 to cause ultrasonic energy at approximately 20 Khz frequency to pass through the ultrasound transmission member 28, thereby causing corresponding ultrasonic vibration of the distal head 104. With the balloon 98 deflated, the operator may elect to move the catheter 12 back and forth slightly to cause the distal head 104 to traverse the entire region of the vasospasm. In other cases, it may be desirable to allow the catheter 12 to remain in a substantially fixed longitudinal position while emitting the vasospasm-treating ultrasound from the distal head 104 of the device 10.

Liquid may be infused through the lumen of the inner tube 60 via the irrigation port 12 to provide a continuous liquid environment around the distal head 104 during the ultrasound vasorelaxation treatment. Also, if necessary, pharmacologic agents may be infused through the lumen of the inner tube 60 via the irrigation port 72.

Thus, as described hereabove, the combination ultrasound ablation/balloon dilation catheter device 10 of the present invention provides enhanced capabilities for ablating and dilating severe occlusions or high grade stenoses. Additionally, unlike other balloon dilation catheters of the prior art, the device 10 of the present invention offers the capability of delivering ultrasound treatment to prevent or reverse vasospasm before, during or immediately after the dilation procedure.

ii. Additional Methods and Devices For Utilizing Ultrasound To prevent Or Treat Vasospasm As described above, the onboard ultrasound ablation component of the ultrasound ablation/balloon dilation catheter device 10 may be utilized in accordance with the vasospasm preventing/treating method of the present invention to prevent or treat the occurrence of vasospasm during the operative procedure. It will be appreciated, however, that the herein described method of preventing or treating vasospasm by delivery of ultrasonic energy to the blood vessel may be accomplished by many other types of devices and is not limited to the above-described combination ultrasound ablation/balloon dilation catheter device 10. Indeed, the present method of preventing or treating vasospasm by delivery of ultrasound may be accomplished by passing an independent or separate ultrasound transmission wire or waveguide through any working lumen of an existing catheter, balloon dilation catheter, laser ablation catheter, atherectomy catheter device or other intravascular catheter or surgical member which has been inserted into the affected blood vessel.

Referring now to FIG. 7, there is shown a catheter device 114 constructed in accordance with a second embodiment of the present invention. Catheter device 114 incorporates combined ultrasound ablation and laser ablation components, and generally comprises an elongate catheter body 116 having a proximal end 118, a distal end 120, and defining an outer surface 122 and an inner luminal surface 124. Mounted on the proximal end 118 of the catheter body 116 is a proximal end connector assembly 126. As with the first embodiment, connected to the proximal end of the connector assembly 126 is an ultrasound transducer 22. Additionally, an ultrasound generator 24 having a foot-actuated on/off switch 26 is operatively connected to the ultrasound transducer 22 so as to send ultrasonic energy through the catheter body 116 when desired.

In the second embodiment, the catheter body 116 is formed from a single lumen tube. Extending longitudinally through the catheter body 116 is an ultrasound transmission member 128 having a proximal end which extends through the connector assembly 126 and is interfaced to the ultrasound transducer 22 in the same manner previously described with respect to the first embodiment. The ultrasound transmission member 128 further includes an enlarged distal end 130 having a distal head 132 mounted thereon. Similar to the distal head 104 previously described with respect to the first embodiment, the distal head 132 comprises a generally round distal portion 134 and a reduced diameter neck or proximal portion 136. In the second embodiment, the outer diameter of the proximal portion 136 is approximately the same as or slightly less than the inner diameter of an annular recess 138 formed within the inner luminal surface 124 of the catheter body 116 adjacent the distal end 120 thereof. In this respect, the proximal portion 136 of the distal head 132 is inserted into the distal end 120 of the catheter body 116 to a point where the distal most tip of the catheter body 116 abuts against the proximal aspect of the distal portion 134 of the distal head 132, as shown. As with the first embodiment, the distal head 132 may be retained within the catheter body 116 via an adhesive or other suitable affixation method. Additionally, formed within the proximal portion 136 of the distal head 132 is a conical depression 140 which is used to direct a guidewire 142 of the catheter device 114 into the guidewire passage aperture 144 formed within and extending longitudinally through the distal head 132. Like the guidewire passage aperture 110, the guidewire passage aperture 144 is sized so as to be slightly larger than the outer diameter of the guidewire 142 to be passed therethrough so as to permit fluid infused into the lumen of the catheter body 116 via an irrigation port 146 of the connector assembly 126 to be infused through the lumen and to pass out of the distal end 120 of the catheter body 116 via the guidewire passage aperture 144, even when the guidewire 142 extends therethrough.

In the second embodiment, the connector assembly 126 is formed in a manner substantially analogous to the connector assembly 20 previously described with respect to the first embodiment. In addition to the irrigation port 146, the connector assembly 126 also includes a guidewire insertion arm 148 as well as a diverter tube disposed therein which is identically configured to the diverter tube 90 to cause the guidewire 142 to be directed through the guidewire insertion arm 148 when such is extended longitudinally through the lumen of the catheter body 116.

Though being substantially identical to the connector assembly 20, the connector assembly 126 of the second embodiment includes, as an alternative to the balloon inflation port 78, a laser energy transmitting member introduction port 150 which is included in approximately the same position as the previously-described balloon inflation port 78. In the second embodiment, introduction port 150 includes a hollow bore extending therethrough which is in communication with the longitudinal bore of the connector assembly 126 as well as the lumen of the catheter body 116. Disposed within and extending longitudinally through the lumen of the catheter body 116 are a plurality of laser energy transmitting members 152 which are inserted into the lumen of the catheter body 116 via the introduction port 150. The laser energy transmitting members 152 each include proximal ends Which are connected to a laser energy transmission source 154 of sufficient energy and absorption characteristics to ablate plaque or other obstructing material such as thrombus. For example, a visible wavelength laser which is highly absorbed by blood components or a near-infrared laser that is highly absorbed by the water component of the obstructing tissue or matter, may be used. The distal ends of the transmitting members 152 extend through the distal head 132 and are substantially flush with the distal aspect of the distal portion 134 thereof. Alternatively, the transmitting member 152 may be distally abutted against a transparent lens cap or window member capable of transmitting or allowing passage therethrough of a preselected wavelength (e.g. a quartz or sapphire lens). Though, as shown in FIGS. 7–10, six laser energy transmitting members 152 are incorporated into the catheter device 114, it will be recognized that greater or fewer numbers of transmitting members 152 may be used. In the second embodiment, the transmitting members 152 comprise optical fibers, though it will be recognized that as an alternative to such optical fibers, other laser energy transmission means, such as a suitable liquid, may be utilized as an alternative. In this respect, if a liquid laser energy transfer medium is utilized, the transmitting members 152 will not be included in the catheter device 114.

In utilizing the catheter device 114 of the second embodiment, the guidewire 142 is initially inserted into the lumen of the blood vessel, with the catheter body 116 being subsequently advanced thereover. Once the distal end 120 of the catheter body 116 is positioned within the blood vessel adjacent the occlusive lesion, the laser energy transmission source 154 is activated thus facilitating the transmission of laser energy out of the distal en 120 via the laser energy transmitting members 152. In the event the exposure of the occluded region of the blood vessel to the laser energy causes a vasospasm to occur, the laser energy transmission source 154 is deactivated, and the ultrasound transducer 22 activated. The activation of the ultrasound transducer 22 oauses ultrasonic energy to be transmitted from the distal end 120 of the catheter body 116 via the ultrasound transmission member 128.

Referring now to FIGS. 11 and 12, as will be recognized, the ultrasound transmission member may be utilized to relax a vasospasm irrespective of whether such is incorporated into a catheter device including balloon dilation, laser ablation or atherectomy ablation components. In this respect, an ultrasound transmission member 300 operatively connected to an ultrasound transducer 22 and corresponding ultrasound generator 24 in the same manner previously discussed with respect to the aforementioned three embodiments of the present invention may be inserted into any conventional connector assembly 302 of a catheter device for purposes of eliminating vasospasm. In this respect, when the catheter body of the catheter device is advanced over the guidewire 304, and a vasospasm occurs as a result of any procedure being conducted within the blood vessel, the guidewire 304 may be removed from within the lumen of the catheter body and replaced with the ultrasound transmission member 300. Thereafter, the ultrasound generator 24 may be activated thereby causing the ultrasound transducer 22 to transmit ultrasonic energy to the distal end of the catheter body via the ultrasound transmission member 300, so as to alleviate the vasospasm. Additionally, the ultrasound transmission member 300 may also be inserted through the lumen of the catheter body without removing the guidewire from there within. As such, for this manner of operation, all that is required is that the connector assembly 302 be adapted to accommodate both the guidewire 304 and ultrasound transmission member 300.

The method of preventing or treating vasospasm in accordance with the present invention may also be utilized in conjunction with any atherectomy catheter or other device for cutting, shaving, grinding and/or aspirating occlusive matter from the lumen of the blood vessel. To effect the delivery of vasorelaxant ultrasound energy in accordance with the invention, an ultrasound transmission member may be passed through or positioned within the elongate body of an atherectomy catheter.

Examples of atherectomy catheters Wherein an ultrasound transmission member 200 may be permanently positioned, or temporarily inserted, to effect vasorelaxation in accordance with the present invention, include those devices described in U.S. Pat. No. 4,765,332 (Fischel) entitled PULLBACK ATHERECTOMY CATHETER SYSTEM, PCT INTERNATIONAL PATENT PUBLICATION NO. WO 89/05611 (Muller) entitled ATHERECTOMY DEVICE WITH ANGIOPLASTY BALOON AND METHOD, EUROPEAN PATENT PUBLICATION NO. 347,098A2 (Shiber) entitled ATHERECTOMY SYSTEM WITH A GUIDEWIRE, U.S. Pat. No. 5,100,423 (Fearnot) entitled ABLATION CATHETER and U.S. Pat. No. 4,924,863 (Sterzer) entitled ANGIOPLASTIC METHOD FOR REMOVING PLAQUE FROM A VAS.

Figure 13:
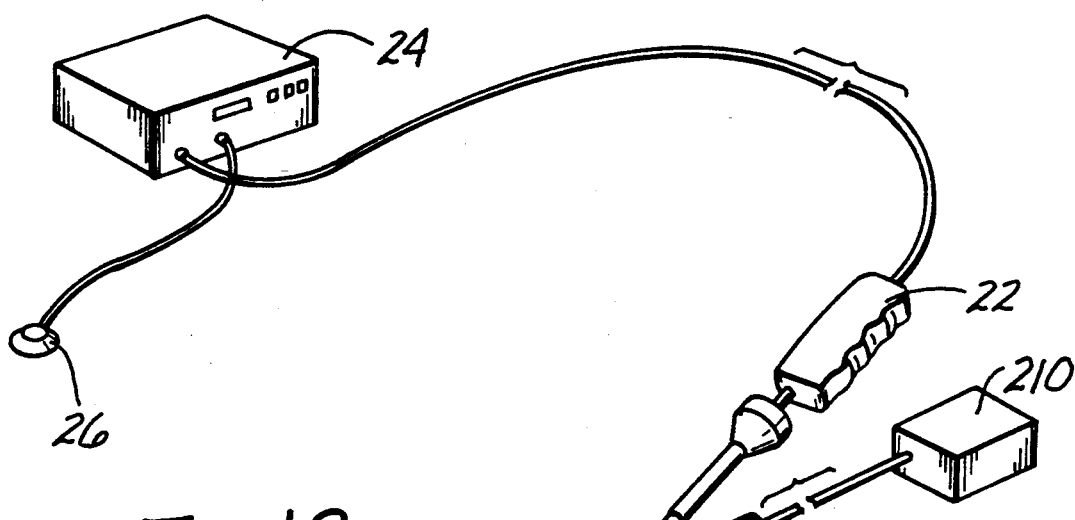
FIG. 13 is a perspective view of an atherectomy catheter device equipped with an ultrasound component for delivering vasorelaxant ultrasound energy during an atherectomy procedure.
Figure 14:
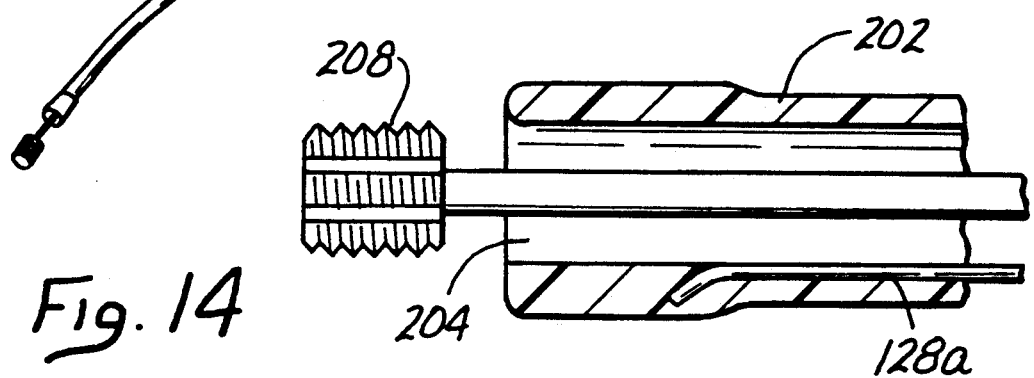
FIG. 14 is an enlarged perspective view of the distal portion of the catheter body designated by the numeral 14 in FIG. 13.

In accordance with the invention, FIGS. 13 and 14 show an atherectomy catheter device 200 comprising an elongate catheter body 202 having a proximal end, a distal end and a lumen 204 extending therethrough. A drive member or shaft 206 extends longitudinally through lumen 204. A cutting or grinding apparatus 208 is mounted on the distal end of driveshaft or member 206. The driveshaft or member 206 is then utilized to operatively manipulate (e.g. rotate and/or longitudinally back and/or forth) the cutting apparatus 208 so as to remove or cut occlusive matter from the blood vessel lumen, immediately ahead of the distal end of the catheter body 202. A power drive unit 210 may be connected to the proximal end of the driveshaft or member 206 to rotate, longitudinally move, or otherfwise drive or energize the driveshaft or member 206 in a manner that will effect the desired cutting movement of the cutting apparatus 208.

A proximal end connection apparatus 212 is formed on the proximal end of the catheter body 202 and incorporates an elongate hollow inner bore which is fluidly consistent with lumen 204 of catheter body 202. A suction/infusion sidearm 214 is formed on the proximal end connector apparatus 212 to permit infusion of fluid in a proximal direction through lumen 204 of catheter body 202 and/or to permit aspiration or withdrawal of fluid, debris or excised occlusive material in a distal direction through the lumen 204 of catheter body 202.

The ultrasound transmission member 128a is connected at its proximal end to ultrasound transducer 22. The ultrasound transducer 22 is connected to the signal generation unit 24. The signal generation unit 24 is actuatable by way of foot pedal 26. A signal generation unit 24 and ultrasound transducer 22 are operative to generate ultrasonic energy within the frequency range of 1-1000 Khz and preferably approximately 20 Khz. Thus, when actuated, ultrasonic energy within the range of 1-1000 Khz and preferably approximately 20 Khz will pass through the ultrasound transmission member 128a to the distal end thereof. The distal end of ultrasound transmission member 128a is affixed to the body of the catheter 202 near the distal end thereof so as to cause ultrasonic end vibation of the distal end of the catheter body 202.

In accordance with the invention, if vasospasm is encountered prior to, during or immediately after the atherectomy procedure, the signal generator 24 and ultrasound transducer 22 may be utilized to send vasorelaxant ultrasound energy through the ultrasound transmission member 128a, causing the distal portion of the catheter body 202 to undergo ultrasonic vibration within the frequency range of 1-1000 Khz and preferrably approximately 20 Khz. Such ultrasonic vibration of the catheter body will result in vasorelaxation or reversal of the vasospasm in the region of blood vessel immediately adjacent the vibrating portion of the catheter body 202. In some embodiments of the invention wherein the driveshaft or member 206 is longitudinally extractable, the cutting apparatus 208 may be extracted into the distal end of the lumen 204 prior to initiation of the ultrasonic vasorelaxant treatment.

Also, in accordance with the invention, the catheter body 202 may be gently moved back and forth to effect the desired ultrasonic vasorelaxant treatment over an extended length of blood vessel wherein the vasospasm is present.

In each of the aforementioned embodiments of the present invention, the catheter bodies 12, 116 may comprise multilumen tubes having at least first and second lumens extending longitudinally therethrough wherein one such lumen is used to accommodate the respective ultrasound transmission member with the second lumen being used as a balloon inflation lumen, laser energy transmitting member passage lumen, or drive member passage lumen.

Although the invention has been described herein with specific reference to presently preferred embodiments thereof, it will be appreciated by those skilled in the art that various additions, modifications, deletions and alterations may be made to such preferred embodiments without departing from the spirit and scope of the invention. Accordingly, it is intended that all reasonably foreseeable additions, deletions, alterations and modifications be included within the scope of the invention as defined in the following claims.

What is claimed is:

1. A method of treating vasospasm during a transluminal balloon angioplasty procedure wherein a catheter having a dilation balloon formed thereon, and at least one lumen extending longitudinally therethrough, has been inserted into the blood vessel, and wherein vasospasm has occurred adjacent the distal end of said catheter, said method comprising the steps of:
   a) inserting an elongate ultrasound transmission member through the lumen of said catheter;
   b) connecting said elongate ultrasound transmission member to an ultrasound generating system operative to generate ultrasound energy within the frequency range of 10-1000 kHz; and, c) passing ultrasonic energy within the frequency range of 10–1000 kHz through said ultrasound transmitting member to effect treatment of said vasospasm adjacent the distal end of said catheter body.

2. The method of claim 1 wherein step (c) specifically comprises:

passing ultrasound having a frequency of approximately 20 Khz through said ultrasound transmission member to effect ultrasonic treatment of the vasospasm adjacent the distal end of said catheter body.

3. The method of claim 1 further comprising:
(d) moving said catheter body back and forth to increase the size of the region of blood vessel to which ultrasonic treatment is delivered.

4. The method of claim 1 further comprising:
(d) moving the ultrasound transmission member back and forth to increase the size of the region of blood vessel to which ultrasonic treatment is delivered.

* * * * *